United States Patent [19]

Lin

[11] Patent Number: 5,423,816
[45] Date of Patent: Jun. 13, 1995

[54] INTERVERTEBRAL LOCKING DEVICE

[76] Inventor: Chih I. Lin, 513 S. Golden Pardos Dr., Diamond Bar, Calif. 10765

[21] Appl. No.: 98,857
[22] Filed: Jul. 29, 1993
[51] Int. Cl.$^6$ .............................................. A61B 17/56
[52] U.S. Cl. ....................................... 606/61; 623/17
[58] Field of Search ....................... 606/61, 72; 623/17

[56] References Cited

U.S. PATENT DOCUMENTS

| 4,309,777 | 1/1982 | Patil | 623/17 |
| 5,055,104 | 10/1991 | Ray | 606/61 |
| 5,123,926 | 6/1992 | Pisharodi | 623/17 |
| 5,320,644 | 6/1994 | Baumgartner | 623/17 |

*Primary Examiner*—Tamara L. Graysay
*Attorney, Agent, or Firm*—Bacon & Thomas

[57] ABSTRACT

An intervertebral locking device comprises one spiral elastic body, two bracing mounts and two sets of locking members. The two bracing mounts are fastened respectively to both ends of the spiral elastic body. The two sets of locking members are fastened respectively with the two bracing mounts such that each set of the locking members is anchored in one of the two vertebrae adjacent to a vertebra under treatment. The spiral elastic body and the vertebra under treatment evince similar elastic qualities, i.e. similar deflection characteristics. A plurality of bone grafts affinitive to the vertebra under treatment are deposited in the chambers of the spiral elastic body and in the spaces surrounding the spiral elastic body.

1 Claim, 3 Drawing Sheets

FIG. 1
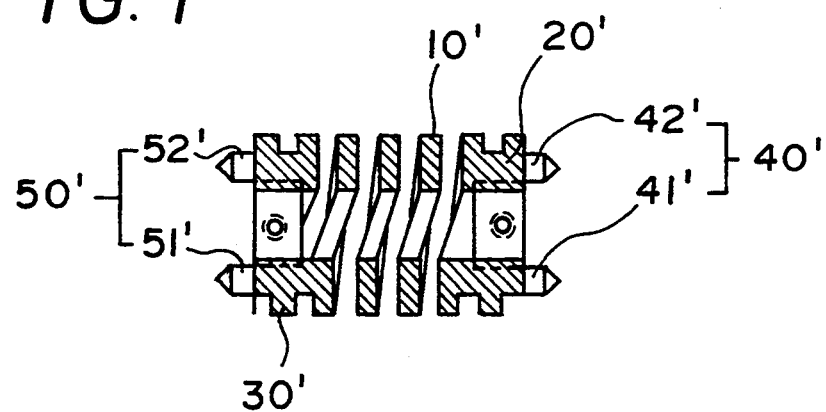
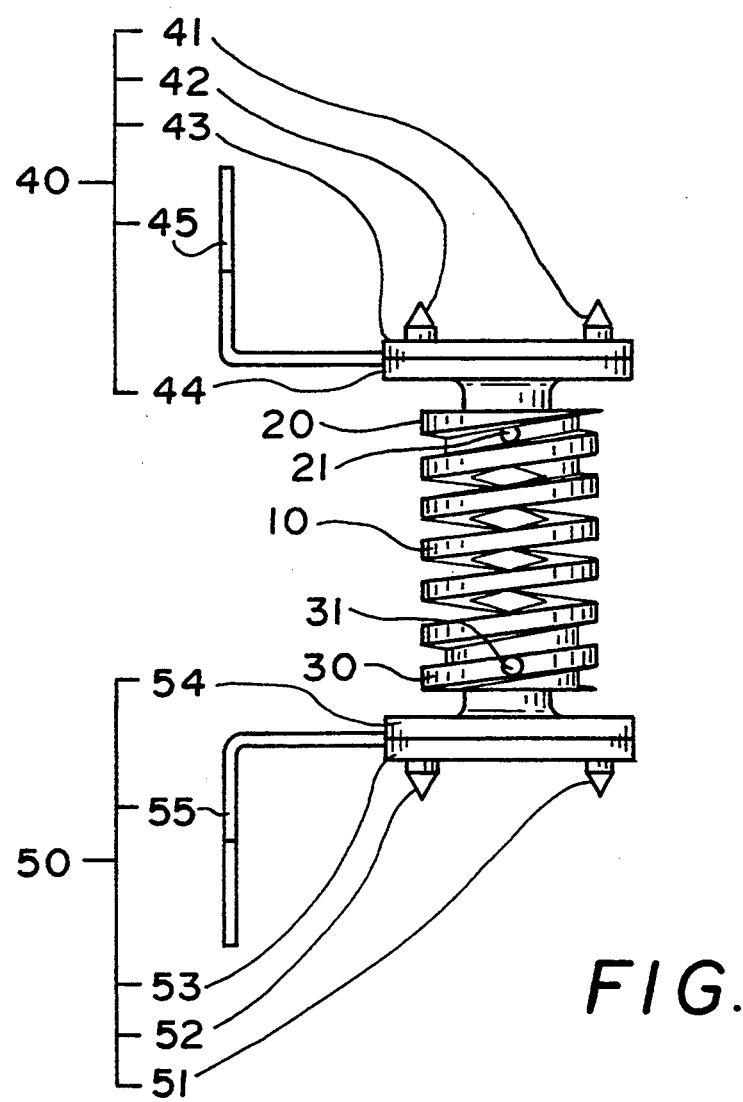
FIG. 2

INTERVERTEBRAL LOCKING DEVICE

FIELD OF THE INVENTION

The present invention relates generally to a spinal orthopedic device, and more particularly to an intervertebral locking device.

BACKGROUND OF THE INVENTION

As exemplified by the spinal fixator made by Spinal Orthopedic Devices, Inc. of the United States and sold under the trademark RAZAIAN, the intervertebral locking device of the prior art, comprised of a structure of steel material, is capable of pulling apart two adjacent vertebrae under treatment so that these two vertebrae are separated from each other by an appropriate interval. Such a prior art locking device as mentioned above is in fact not suitable for use in an orthopedic surgery for treating deformities, diseases, and injuries of the vertebrae in view of the fact that the vertebrae have various curvatures. In addition, the steel structure of the prior art spinal fixator described above is known to have a deflection characteristic, which is five to twenty times greater than those of the vertebrae. As a result, the mechanical stress exerting on the vertebrae under treatment is imparted almost entirely to the steel structure of the spinal fixator, thereby resulting in poor contact between the bone graft and the vertebrae under treatment. The formation of new bone is therefore undermined to an extent that the effect of the treatment is substantially compromised, and that the healed vertebrae are susceptible to a side effect which brings about a shrinkage of the vertebrae in question.

SUMMARY OF THE INVENTION

It is, therefore, the primary objective of the present invention to provide an intervertebral locking device with a spiral elastic body having a quantity of deflection which approximates the deflection characteristics of the vertebrae.

It is another objective of the present invention to provide an intervertebral locking device with a spiral elastic body having a specific deflection characteristic.

It is still another objective of the present invention to provide an intervertebral locking device which is composed of a spiral elastic body, two bracing mounts and two sets of locking members.

The foregoing objectives and features of the present invention are attained by an intervertebral locking device comprising a spiral elastic body, two bracing mounts, and two locking members. The spiral elastic body has an associated deflection characteristic, which can be altered by adjusting the roughness of the spiral lines, the material quality of the elastic body and the spiral moment. The spiral elastic body of the present invention is therefore compatible with respect to the deflection characteristics of the vertebrae, thereby resulting in an excellent contact between the locking members of the present invention and the vertebrae under treatment. In addition, the spiral elastic body of the present invention brings about an excellent intervertebral formation of new bone and prevents a shrinkage of the healed vertebrae.

The foregoing objectives and features of the present invention will be better understood by studying the following detailed description of the present invention in conjunction with the drawings provided herewith.

BRIEF DESCRIPTION OF THE DRAWINGS

FIG. 1 shows a sectional view of a first preferred embodiment of the present invention.

FIG. 2 shows a schematic view of a second preferred embodiment of the present invention.

FIG. 3a is a an end view of an adjusting rod incorporated in the embodiment of FIG. 2.

FIG. 3b is a side view of the adjusting rod of FIG. 3a.

DETAILED DESCRIPTION OF THE INVENTION

Figures 3A, 3B:
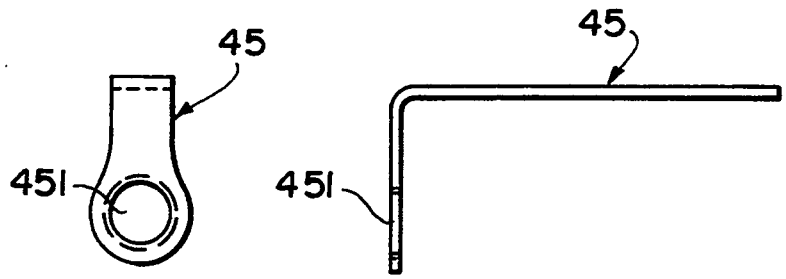

Referring to FIG. 1, an intervertebral locking device of the present invention is shown to comprise a spiral elastic body 10', two bracing mounts 20' and 30', and two locking members 40' and 50'.

By adjusting the roughness of the spiral lines, the material quality and the spiral movement of the spiral elastic body 10', the deflection characteristics of the spiral elastic body 10' can be so changed as to approximate the elasticity or deflection characteristics of the vertebrae intended to be treated. The spiral elastic body 10' is made of any biocompatible iron-based elastic material, such as stainless steel 316LVM, or of any biocompatible titanium-based elastic material, such as Ti-6-4, or of any biocompatible elastic cobalt-molybdenum-nickel alloy, etc.

The bracing mounts 20' and 30' are made integral with the spiral elastic body 10' and are connected respectively with both ends of the spiral elastic body 10'. The bracing mount 20' has an outer side which is fastened with the locking member 40' while the bracing mount 30' has an outer side that is fastened with the locking member 50'. The locking member 40' is provided with a plurality of projections 41' and 42' having sharp tips while the locking member 50' is provided with a plurality of projections 51' and 52' also having sharp tips as shown in FIG. 1. The locking members 40' and 50' of the first preferred embodiment of the present invention are basically similar in structure and function to those which are used commonly in the prior art, such as the locking member discussed above. It is suggested that a specialized locking member, which is disclosed in co-pending U.S. patent application of this inventor, may be used. In the first preferred embodiment of the present invention, the bracing mounts 20' and 30', and the locking members 40' and 50' are made integrally with the spiral elastic body 10'. However, the bracing mounts and the locking members may be joined together by other means which are used commonly in the prior art.

It must be noted here that the term "outer side" mentioned above refers to the side which is located along the axial line of the spiral elastic body 10' and which is located away from the center point of the axial line.

As shown in FIG. 2, the second preferred embodiment of the present invention comprises a spiral elastic body 10, two bracing mounts 20 and 30, and two locking members 40 and 50. The locking member 40 is composed of two projections 41 and 42 having painted tips, a stopping plate 43, a base 44 and an adjusting rod 45. Similarly, the locking member 50 is made up of two projections 51 and 52 having pointed tips, a stopping plate 53, a base 54 and an adjusting rod 55. The bracing mounts 20 and 30 are provided respectively with threaded holes 21 and 31 for use in fastening the bracing mount 20 and the base 44 of the locking member 40, and for use in fastening the bracing mount 30 and the base 54 of the locking member 50.

Figures 3C, 3D, 3E:
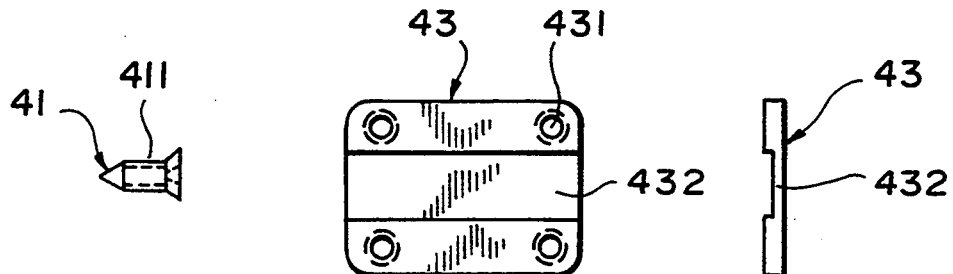
FIG. 3c is a side view of an attachment projection incorporated in the embodiment of FIG. 2.
FIG. 3d is a bottom view of a stopping plate incorporated in the embodiment of FIG. 2.
FIG. 3e is a side view of the stopping plate of FIG. 3d.
Figures 3F, 3G, 3H:
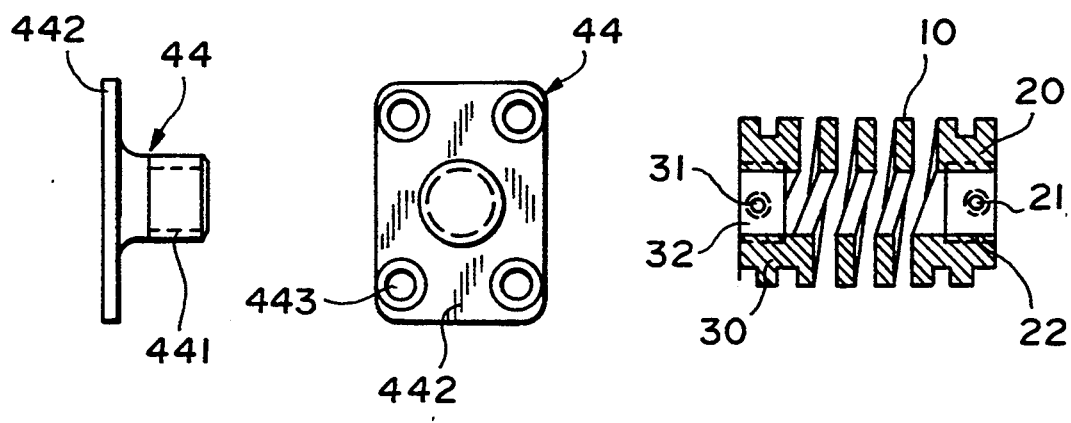
FIG. 3f is a side view of a base portion of a locking member incorporated in the embodiment of FIG. 2.
FIG. 3g is a top view of the base portion of the locking member incorporated in the embodiment of FIG. 2.
FIG. 3h is a cross-sectional view of a spiral elastic body incorporated in the embodiment of FIG. 2.

As shown in FIGS. 3a and 3b, the adjusting rod 45 is provided with a through hole 451. The projection 41 defines a threaded projection 411, as shown in FIG. 3c. The stopping plate 43 is provided with a plurality of threaded holes 431 and with a centrally located slot 432 facing toward the center point of the axial line of the spiral elastic body 10, as shown in FIGS. 3d and 3e. Referring to FIGS. 3f and 3g, the base 44 is shown to comprise an outer threaded projection 441, a flat plate 442, and a plurality of bevel through holes 443, with each of the bevel through holes 443 having a diameter facing toward the center point of the axial line of the spiral elastic body 10 and being located between the diameter of the threaded head and the diameter of the threaded projection, and with each of the bevel through holes 443 having a diameter facing away from the center point of the axial line of the spiral elastic body 10 and corresponding to the diameter of the threaded projection. As shown in FIG. 3h, the spiral elastic body 10 and the two bracing mounts 20 and 30 are made integrally, with the bracing mounts 20 and 30 being provided with the inner threaded projections 22 and 32. In the second preferred embodiment of the present invention, the threaded projection 441 of the base 44 engages the inner threaded projection 22 of the bracing mount 20. A small screw (not shown in the drawing) is screwed into the threaded hole 21 of the bracing mount 20 so as to fasten securely the base 44 and the bracing mount 20. The stopping plate 43 is placed on the flat plate 442 of the base 44 such that the threaded holes 431 are aligned with the bevel through holes 443 of the flat plate 442. In the meantime, the adjusting rod 45 is inserted into the slot 432 of the stopping plate 43 so that the adjusting rod 45 is located between the flat plate 442 of the base 44 and the stopping plate 43. The stopping plate 43 is fastened securely to the base 44 by means of the projection 41 which engages the threaded hole 431 of the stopping plate 43 via the bevel through hole 443 of the flat plate 442.

Figure 4:
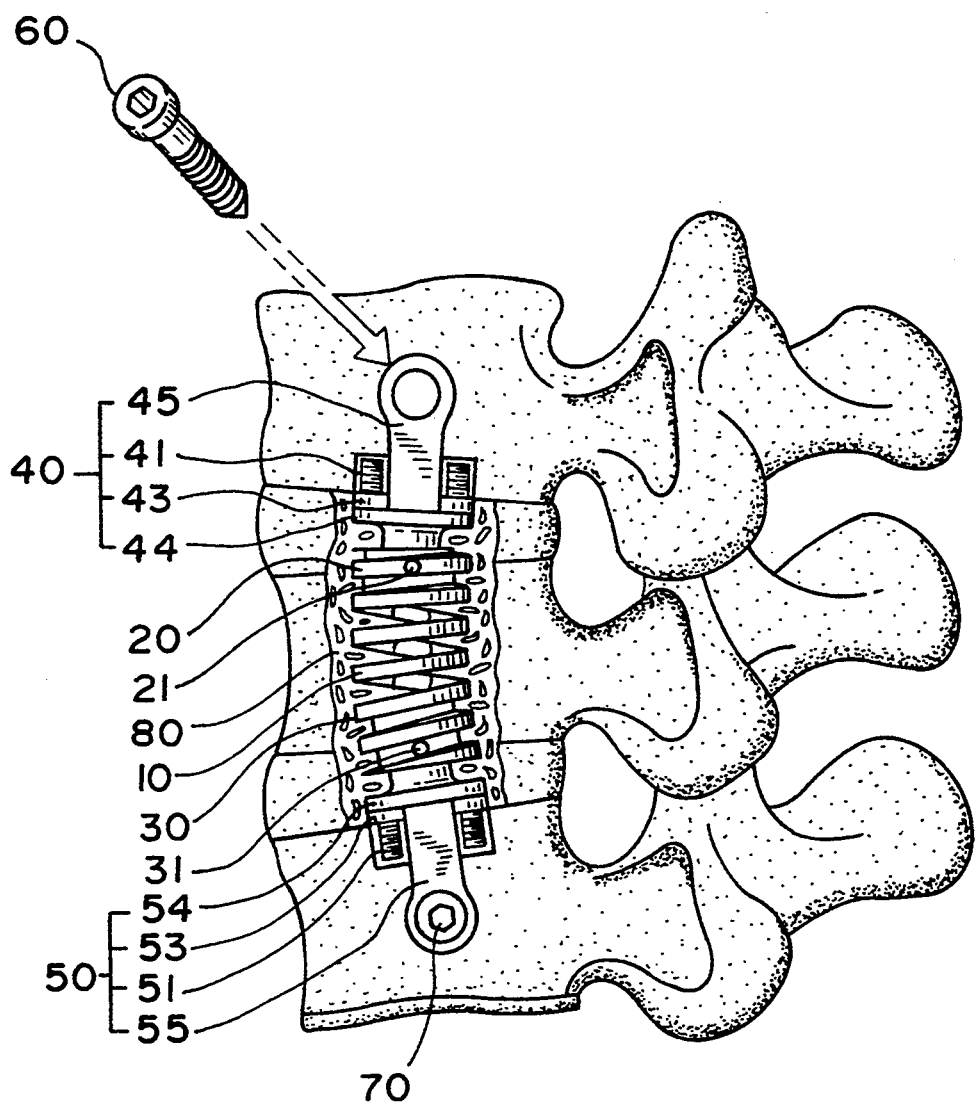
FIG. 4 shows a schematic view of the second preferred embodiment of the present invention as shown in FIG. 2 implanted between vertebrae.

As shown in FIG. 4, the projections 41 and 51 of the implanted interverbral locking device of the second preferred embodiment of the present invention are lodged in the cavities of the two vertebrae under treatment. The vertebrae are then further fixed by means of two bolts 60 and 70, which are anchored securely in the vertebrae via the through holes 451 and 551 of the adjusting rods 45 and 55. A number of bone grafts 80 are disposed in the chambers of the spiral elastic body 10 and in the spaces between the intervertebral locking device and the vertebrae. The bone grafts 80 may be grafted from a natural bone affinitive to the vertebrae under treatment. The synthetic grafts, such as those sold under the trademark BIOCERAM made by Kyocera Corporation of Japan, may be also used as the bone grafts 80. Such synthetic grafts must be also affinitive to the vertebrae under treatment. The surgical procedures of implanting the intervertebral locking device of the present invention are similar to those of implanting the intervertebral locking device of the prior art.

The embodiments of the present invention described above are to be regarded in all respects as merely illustrative and not restrictive. Accordingly, the present invention may be embodied in other specific forms without deviating from the spirit thereof. Therefore, the present invention is to be limited only by the scope of the following appended claims.

What is claimed is:

1. An intervertebral locking device for use in treating vertebrae comprising:

a single spiral elastic body, said spiral elastic body having associated deflection characteristics substantially the same as deflection characteristics associated with a vertebra to be treated;

a pair of bracing mounts, each of said bracing mounts being fastened to a respective end of said spiral elastic body;

two sets of locking members fastened to said pair of bracing mounts respectively, each set of said two sets of locking members being adapted to be anchored in one of two vertebrae adjacent to a vertebra to be treated; and said single spiral elastic body forming a chamber means therein for receiving a plurality of bone grafts affinitive to a vertebra to be treated, whereby additional bone grafts may be receivable in spaces surrounding said spiral elastic body.

* * * * *